(12) United States Patent
Dioguardi

(10) Patent No.: US 6,270,750 B1
(45) Date of Patent: *Aug. 7, 2001

US006270750B1

(54) PROLINE-, GLYCINE- AND LYSINE-BASED PHARMACEUTICAL COMPOSITION USEFUL IN DENTAL TREATMENT BOTH IN THE INJECTABLE FORM AND IN THE FORMULATION FOR TOPICAL USE

(75) Inventor: Francesco Dioguardi, Milan (IT)

(73) Assignee: Solartium Establishment, Vaduz (LI)

( * ) Notice: Subject to any disclaimer, the term of this patent is extended or adjusted under 35 U.S.C. 154(b) by 0 days.

This patent is subject to a terminal disclaimer.

(21) Appl. No.: 09/459,767

(22) Filed: Dec. 13, 1999

(30) Foreign Application Priority Data

Dec. 18, 1998 (IT) ................................ MI98A2746

(51) Int. Cl.⁷ ......................... A61K 7/22; A61K 31/195
(52) U.S. Cl. ............................. 424/54; 424/319
(58) Field of Search ........................ 424/54, 319

(56) References Cited

U.S. PATENT DOCUMENTS

| | | | |
|---|---|---|---|
| 4,968,590 | * 11/1990 | Kuberasampath et al. | 530/326 |
| 5,011,691 | * 4/1991 | Uppermann et al. | 424/423 |
| 5,198,465 | 3/1993 | Dioguardi | 514/474 |
| 5,369,142 | * 11/1994 | Culbertsen et al. | 523/116 |
| 5,653,984 | * 8/1997 | Fodor et al. | 424/776 |
| 5,840,325 | * 11/1998 | Kuberasampath et al. | 424/420 |
| 5,958,441 | * 9/1999 | Uppermann et al. | 424/443 |

FOREIGN PATENT DOCUMENTS

| | | | |
|---|---|---|---|
| 5717909A | * 10/1982 | (JP) . | |
| WO9627371 | 12/1996 | (WO) | A61K/31/195 |
| 9826774A1 | * 6/1998 | (WO) . | |

* cited by examiner

Primary Examiner—Shep K. Rose
(74) Attorney, Agent, or Firm—Abelman, Frayne & Schwab

(57) ABSTRACT

Pharmaceutical composition comprising as essential ingredients proline, lysine and glycine, suitable for the dental treatment of various periodontal diseases, based upon the local injection of an aqueous solution of the composition itself or on the topical application of its formulations, such as mouth-washes, toothpastes, and gengival gels.

6 Claims, No Drawings

PROLINE-, GLYCINE- AND LYSINE-BASED PHARMACEUTICAL COMPOSITION USEFUL IN DENTAL TREATMENT BOTH IN THE INJECTABLE FORM AND IN THE FORMULATION FOR TOPICAL USE

SUMMARY

The present invention regards the preparation of pharmaceutical compositions substantially based on proline, glycine and lysine, capable of promoting proliferation of fibroblasts with production of collagen, in the treatment of periodontal diseases, both in the form of injectable solution and in the form of a mouth-wash, toothpaste, or gengival gel.

PRIOR ART

The U.S. Pat. No. 5,198,465 describes a proline-, glycine- and lysine-based composition, possibly also comprising methionine, cysteine, Vitamin C and other ingredients, the said composition being capable of inducing or promoting the biological synthesis of collagen in the situations in which this synthesis is deficient. According to this document of the prior art, the above composition, in which the essential amino acids, i.e., proline, glycine and lysine, are present in specific weight ratios to one another, can be formulated with diluents and excipients of an oily type or not, in a form suitable for external topical use, or else it is formulated suitably for oral administration.

DETAILED DESCRIPTION OF THE INVENTION

The purpose of the present invention is to produce a pharmaceutical composition basically comprising proline, glycine and lysine, suitable for dental therapy based on the use of the composition as a mouth-wash, toothpaste, gengival gel, or else as a solution that may be locally injected, for the treatment of various forms of periodontal disease.

In addition to the above-mentioned essential amino acids, the composition may also contain other amino acids useful for achieving the desired result of promoting the biological synthesis of collagen locally. These different amino acids, which may be present in percentages of up to 70% of the total, are particularly useful in the case of nutritional deficiencies.

The amino acids which are used in experimentation and which are considered in the present description are those of the laevorotatory type, which thus correspond to the natural products that are to be considered the active form; however, also the racemic form can exert the same activity, albeit to a proportionally lesser extent.

As a general rule, the amounts of the amino acids in the composition fall within the following limits:

| | |
|---|---|
| proline | from 10 wt % to 50 wt % |
| glycine | from 10 wt % to 50 wt % |
| lysine | from 4 wt % to 20 wt % |
| leucine | from 0 wt % to 20 wt % |
| methionine and/or cysteine and/or cystine, all together | from 0 wt % to 20 wt % |
| α-ketoglutaric acid | from 0 wt % to 20 wt % |

In view of the dental treatment at which the product is aimed, also other ingredients may be useful in the basic composition as adjuvants in the formation of bone tissue, such as calcium and fluorine compounds, and phosphates.

In addition, in many cases the presence of Vitamin C in quantities of from 10% to 50% of the total is advantageous. Vitamin C works in particular as co-enzyme of hydroxylase in the catalysis of the biological synthesis of collagen.

The injectable aqueous solution can be advantageously prepared extemporaneously by dissolving the composition according to the invention, previously prepared in the lyophilized form, in a biologically compatible aqueous liquid (distilled water, physiological solution or other aqueous solution).

Lyophilization of the Product

The amino acids are dissolved one after another in distilled water; in the clear solution the pH is controlled and is brought, if necessary, to a value of between 6 and 6.4.

The solution obtained, containing from approximately 6 wt % to 8 wt % of total amino acids, is frozen for approximately 10 hours in the lyophilizer at a temperature of −35° C. The frozen product is subjected to a vacuum pressure of at least 80 μHg.

Lyophilization is then carried out according to the following parameters:

temperature of the fluid in boiler: +20° C.

temperature of the fluid in circulating pump: +22° C.

heating timer (set at 5 hours to reach the temperature of the fluid)

heating with a single heating element, under vacuum.

After approximately 19 hours, the temperature of the product reaches +1.4 to +9.6° C. The heating element is then turned off and cold fluid is introduced into the boiler, with regulation of the temperature of the fluid at +42° C. and of the circulating pump at +45° C.

The product is kept for 18 hours at the values indicated above, under vacuum conditions.

Product Used for In Vitro and In Vivo Experimentation

A product was used, the essential components of which were:

| | | |
|---|---|---|
| L-proline | 375 parts by weight ~ | 40.8 wt % (*) |
| L-lysine | 95 parts by weight ~ | 10.3 wt % |
| L-glycine | 450 parts by weight ~ | 48.9 wt % |

(*) percentages of the individual amino acids over total amino acids

This product is identified here and in the sequel with the code SC.1200. The composition of amino acids according to the invention has proved very effective in dental therapy for the treatment of various periodontal conditions. A topical treatment was carried out with local injections of small amounts (from 0.5 to 2 ml) of injectable aqueous solution containing quantities in the region of from 0.05 to 0.1 g of the composition in question.

Excellent results have been obtained in the treatment of gengival sacs, as well in the treatment following on tooth extraction, both for healing of the wound in the mucosal membrane and for the formation of re-growth bone tissue.

In Vitro Tests

Cultures of human fibroblasts deriving from skin tissue of the same cell strain were compared in standard culture medium conditions (RPMI 1640+10% bovine foetal serum, antibiotics) with cultures also treated with various concentrations of SC.1200 corresponding to $1/50$ and $1/100$ concentrations of a 5% mother liquor.

The number of fibroblasts and the production of type I and type III collagen were higher than those found in the control group to a significant extent both at 48 hours ($p<0.02$) and at 72 hours ($p<0.01$).

Calculating the ratio of collagen production for each individual fibroblast, a datum was obtained that approximately coincided in the three groups, thus witnessing to the fact that the synthesis induced by SC.1200 is not outside the physiological limits, but is an increment per unit time, which is followed by a faster duplication of the fibroblasts that have available SC.1200, and hence a larger amount of end product.

In Vivo Tests

Injectable Solution

A solution of 0.1 g of SC.1200 in 1–2 ml of physiological solution was used in various periodontal diseases in subjects of different ages. The experimentation carried out on 15 patients affected by periodontal conditions was based on the use in the same patient of injections of SC.1200 and, for purposes of comparison, of injections of physiological solution in gengival sacs of similar dimensions.

In these patients, with voluminous gengival sacs, of depth$\geq$3 mm<5 mm, local applications were made, varying in number from 1 to 3, after prior local curettage. A check was carried out, using a calibrated probe, before each individual application and fifteen days after each application. After one single application of SC.1200, the reduction in the depth of the sac was 1–3 mm, whereas no reduction was found with the physiological solution used for comparison. In the cases of multiple applications, after approximately 6 weeks the sacs disappeared completely in 5 cases out of 8, with an average reduction in the size of the sacs of over 70% in the remaining cases ($p<0.001$ with the paired t-test). In the sacs treated with physiological solution, no improvement could be detected, and after 60 days of treatment, the injection therapy was suspended.

Applications were also made in seats of avulsion of supernumerary teeth or third molars, and total recovery of the radio-opaque matrix, together with a probe measurement of zero, was found after as few as fifteen days from application. A particularly remarkable datum was the rapidity with which the wounds in the mucous membranes closed. In a number of cases (nearly 70%), it was possible or necessary to remove the surgical stitches after less than 7 days (as against 10, which is the average in similar cases). In addition, in a limited number of cases (5 cases), the product was used as last resort in individuals who had undergone implantation procedures which had failed on account of atrophy of the mandibular or maxillary bone. In 3 cases out of 5 there was a complete re-growth of the bone (defined as "unaccountable in the light of current knowledge" by the operator), and in two cases bone damage was more than halved. In 3 cases of high mobility of teeth overlying atrophic bone structures, two applications at an interval of approximately 7 days restored complete stability to the tooth, thus rendering the planned extraction and subsequent implantation of a prosthesis needless.

Biopsy of the newly formed tissue was then carried out in five cases of volunteers who had undergone the treatment and who, upon x-ray examination, presented disappearance of the sac, a probe measurement of zero, and opacity of the treated site as for deposition of bone tissue. The appearance was observed of a newly formed collagen tissue presenting a trabecular-type structure, which was partly calcific, numerous fibroblasts among newly formed vessels, and a surprisingly high number of osteoblasts presenting colouring characteristics such as to suggest their origin from gengival fibroblasts.

It may be inferred that the strong synthetic stimulation induced by SC.1200 brought about two distinct phenomena: the synthesis in considerable quantities of new collagen in former cavities or in conditions of low presence of bone protein matrix (in all cases type III collagen), and the capacity of the fibroblasts to convert, under adequate conditions of stimulation, the SC.1200 and the minerals constantly and abundantly present in saliva (calcium in particular) into cells capable of transforming collagen into bone tissue. This capacity would account for the presence of intra-articular calcification or calcifications present in parenchymal organs as a secondary effect of traumas and consequent repair processes.

Toothpaste

Experiments were carried out applying toothpaste containing 2% SC.1200 in patients suffering from periodontal diseases.

These were 28 subjects of both sexes who presented periodontosis with gengival sacs less than 3 mm in depth and a stabilized clinical picture.

The subjects were randomly divided into two groups of 14 patients. In the first group, a toothpaste not containing amino acids was used twice a day. In the other group the same toothpaste was used containing the amino acids of the present invention.

After two months of treatment, the effect of the therapy on the periodontal affections was assessed using a semiquantitative scale in which the score 1 corresponded to a clear improvement, the score 2 corresponded to a readily assessable improvement, and the score 3 corresponded to a slight improvement or no effect at all.

After this assessment, the treatments were reversed for the two groups of patients, and after a further two months, the same therapeutic evaluation was made.

Table 1 gives the mean values of the scores found after the different treatments at the two control times, i.e., after 60 days and 120 days of therapy.

It emerges clearly how the use of the toothpaste containing 2% of SC.1200 twice a day carried out using the same toothbrushes and for the minimum duration of 5 minutes per intervention is able to bring about a significant improvement in the periodontal condition, and in particular is able to favour renewal of gengival trophism with disappearance of the sacs in many patients.

TABLE 1

| | Duration of treatment | |
|---|---|---|
| | 60 days | 120 days |
| Group A, 14 patients, average score: | 2.64 | 1.57 (°) |
| Group B, 14 patients, average score: | 1.64 (°°) | 2.28 |

Group A: treated in the first 60 days with toothpaste not containing amino acids Group B: treated in the first 60 days with toothpaste containing sc.1200

From day 61 to day 120 the treatment of the two groups was reversed.

(°) and (° °) significant differences as compared to the treatment with toothpaste containing amino acids ($p<0.05$ with $\chi^2$ test)

What is claimed is:

1. A pharmaceutical composition comprising as essential ingredients proline, lysine and glycine, suitable for the dental treatment of various periodontal diseases, in the form of formulations for topical application consisting of: injectable aqueous solutions, mouth-washing solutions, tooth pastes, and gingival gels, in which composition the three amino acids are present in amounts corresponding to the following weight percentages on the whole composition: proline, from 10 wt % to 50 wt % glycine, from 10 wt % to 50 wt %; lysine, from 4 wt % to 20 wt %.

2. Compositions according to claim 1 also containing other supplementary amino acids in a quantity of up to 70% of the total amino acids.

3. Compositions according to claim 2, in which the supplementary amino acids are chosen from among: leucine, methionine, cysteine, cystine, valine, and α-ketoglutaric acid.

4. Pharmaceutical composition according to claim 1 in the form of a lyophilized product suitable for the extemporaneous preparation of an injectable solution.

5. Composition according to claim 1, wherein the injectable solution also contains Vitamin C.

6. Therapeutic treatment of periodontal diseases through topical application of gingival gels, mouth-washing solutions or tooth pastes according to claim 1.

* * * * *